United States Patent
Lodge

(10) Patent No.: US 11,395,878 B2
(45) Date of Patent: Jul. 26, 2022

(54) INJECTION DEVICE AND METHOD OF MAKING AND USING THE SAME

(71) Applicant: Daphne Lodge, Franklin, TN (US)

(72) Inventor: Daphne Lodge, Franklin, TN (US)

( * ) Notice: Subject to any disclaimer, the term of this patent is extended or adjusted under 35 U.S.C. 154(b) by 144 days.

(21) Appl. No.: 16/355,330

(22) Filed: Mar. 15, 2019

(65) Prior Publication Data

US 2020/0289752 A1 Sep. 17, 2020

(51) Int. Cl.
*A61M 5/19* (2006.01)
*A61M 5/20* (2006.01)
(Continued)

(52) U.S. Cl.
CPC ............ *A61M 5/19* (2013.01); *A61M 5/2066* (2013.01); *A61M 5/31596* (2013.01); *A61M 5/3294* (2013.01); *A61M 2209/082* (2013.01)

(58) Field of Classification Search
CPC .. A61M 5/19; A61M 5/2066; A61M 5/31596; A61M 5/3294; A61M 5/3257;
(Continued)

(56) References Cited

U.S. PATENT DOCUMENTS 3,552,394 A * 1/1971 Horn ........................ A61M 5/19
604/173
5,876,380 A * 3/1999 Manganini ............ A61M 5/001
604/191

(Continued)

FOREIGN PATENT DOCUMENTS

KR 20170052782 A 5/2017
WO WO2009145447 A1 12/2009
(Continued)

OTHER PUBLICATIONS

"Innoject, Inc. Is Now Pharma-Pen, Inc.," Market Wired, marketwired. com, Apr. 11, 2005. http://www.marketwired.com/press-release/innoject-inc-is-now-pharma-peninc-659594.htm Discloses an single-use, automatic injection system for drugs and biologics which is activated by depressing a button, wherein the device "automatically extends the needle to a pre-determined depth, injects the liquid, and withdraws the needle back into the interior of the device.".

(Continued)

*Primary Examiner* — James D Ponton
(74) *Attorney, Agent, or Firm* — Stites & Harbison PLLC; Richard S. Myers, Jr.

(57) ABSTRACT

Provided herein are an injection device and a method of injecting a patient. The injection device includes a base portion including a body section and a control section, at least one bracket secured to the body section, an articulation element secured to the control section, and a pusher plate coupled to the articulation element, wherein the articulation element moves the pusher plate with respect to the base portion. The method includes positioning at least two syringes in the injection device, placing an injection end of the injection device in contact with an injection site on the patient, and activating the articulation element, wherein activating the articulation element moves the pusher plate towards the at least two syringes, depressing a plunger and dispensing a fluid from the at least two syringes.

18 Claims, 8 Drawing Sheets

(51) Int. Cl.
*A61M 5/315* (2006.01)
*A61M 5/32* (2006.01)

(58) Field of Classification Search
CPC ............ A61M 5/326; A61M 2209/082; A61M 2005/2013; A61M 2005/208; A61M 5/16827
See application file for complete search history.

(56) References Cited

U.S. PATENT DOCUMENTS

| | | | |
|---|---|---|---|
| 6,468,247 | B1 | 10/2002 | Zamoyski |
| 6,789,467 | B2 | 9/2004 | Johnston et al. |
| 6,840,921 | B1* | 1/2005 | Haider ................ A61M 5/19 604/191 |
| 7,422,574 | B2 | 9/2008 | Eriksson et al. |
| 8,257,582 | B2 | 8/2012 | Angel et al. |
| 8,257,324 | B2 | 9/2012 | Prausnitz et al. |
| 8,666,487 | B2 | 3/2014 | Kang |
| 9,205,202 | B2 | 12/2015 | Bahrami et al. |
| 9,289,605 | B2 | 3/2016 | Choi |
| 9,308,330 | B2 | 4/2016 | Waldman et al. |
| 9,457,183 | B2 | 10/2016 | Sallberg et al. |
| 9,636,458 | B2 | 5/2017 | Hoffman et al. |
| 2005/0027240 | A1* | 2/2005 | Fehr .................... A61M 5/19 604/82 |
| 2006/0211982 | A1* | 9/2006 | Prestrelski ........... A61K 38/27 604/60 |
| 2007/0038181 | A1 | 2/2007 | Melamud et al. |
| 2007/0088268 | A1* | 4/2007 | Edwards ........... A61M 5/2033 604/136 |
| 2008/0255520 | A1* | 10/2008 | Henderson ........... A61M 5/19 604/191 |
| 2010/0030152 | A1 | 2/2010 | Lee et al. |
| 2011/0218497 | A1 | 9/2011 | Assaf |
| 2012/0130207 | A1 | 5/2012 | O'dea et al. |
| 2012/0245560 | A1* | 9/2012 | Hochman ........... A61M 5/1452 604/518 |
| 2014/0088502 | A1 | 3/2014 | Matheny et al. |
| 2015/0133866 | A1 | 5/2015 | Sumida et al. |
| 2015/0141954 | A1 | 5/2015 | Da et al. |
| 2016/0175408 | A1 | 6/2016 | Chang et al. |
| 2017/0007812 | A1 | 1/2017 | Onozuka et al. |
| 2017/0165434 | A1 | 6/2017 | Wang |

FOREIGN PATENT DOCUMENTS

| | | |
|---|---|---|
| WO | WO2016022865 A1 | 2/2016 |
| WO | WO2014142970 A9 | 8/2016 |
| WO | WO2017054009 A1 | 3/2017 |

OTHER PUBLICATIONS

"Products: Advanced dosing technology," data physics, dataphysics. de, Jan. 10, 2016. https://web.archive.org/web/20160110020343/http://www.dataphysics.de/2/st art/products/oca-accessory-range/liquid-dosing-systems/ Discloses an electronic syringe module for use with a direct dosing system which allows software control of dosing volume and rate (Electronic syringe module ESr and ESr-D).

"Multi-Injectors, circular, 5-needle connections, 27G/0.40x4mm, 36pcs.," Mesoram®, mesoram.com, Jun. 28, 2017 https://web.archive.org/web/20170628160112/http://www.mesoram.com/multi-injectors/multi-injectors-circular-5-needle-connections-27g-0-40x4mm-36pcs Discloses a multi-injector syringe featuring multiple needles for various treatment methods, wherein "a standard luer connection allows an easy connection with the drug-containing syringe.".

"Histogen Multiple Needle Injection System," Histogen, beweb. ucsd.edu, Sep. 8, 2012 http://beweb.ucsd.edu/courses/seniordesign/projects/2011/project_20/product.html Discloses a prototype of an injection system to "facilitate the therapeutic delivery of Histogen's Hair Stimulating Complex (HSC)", which features "a luer lock needle head featuring two rows of needles, ten needles per row that is able to fit on any standard syringe.".

"Pumps: Precise, Pulsation-Free, Expandable," Cetoni, cetoni.de, Jul. 15, 2017 https://web.archive.org/web/20170715040137/https://www.cetoni.de/en/products/pumps/ Discloses the neMESYS pump featuring motors inside the pump move the syringe piston, wherein the system follows a modular design concept which can combine multiple pumps.

"What We Do: Hair Rejuvenation," RYSE, rysewellness.com, Jul. 15, 2017 https://web.archive.org/web/20170715043359/http://www.rysewellness.com/hair-rejuvenation/ Discloses a micro-needling and PRP service which uses a "sterile needle-tip containing 12 tiny micro-needles to create controlled micro-injuries to the skin" (What is Micro-Needling).

* cited by examiner

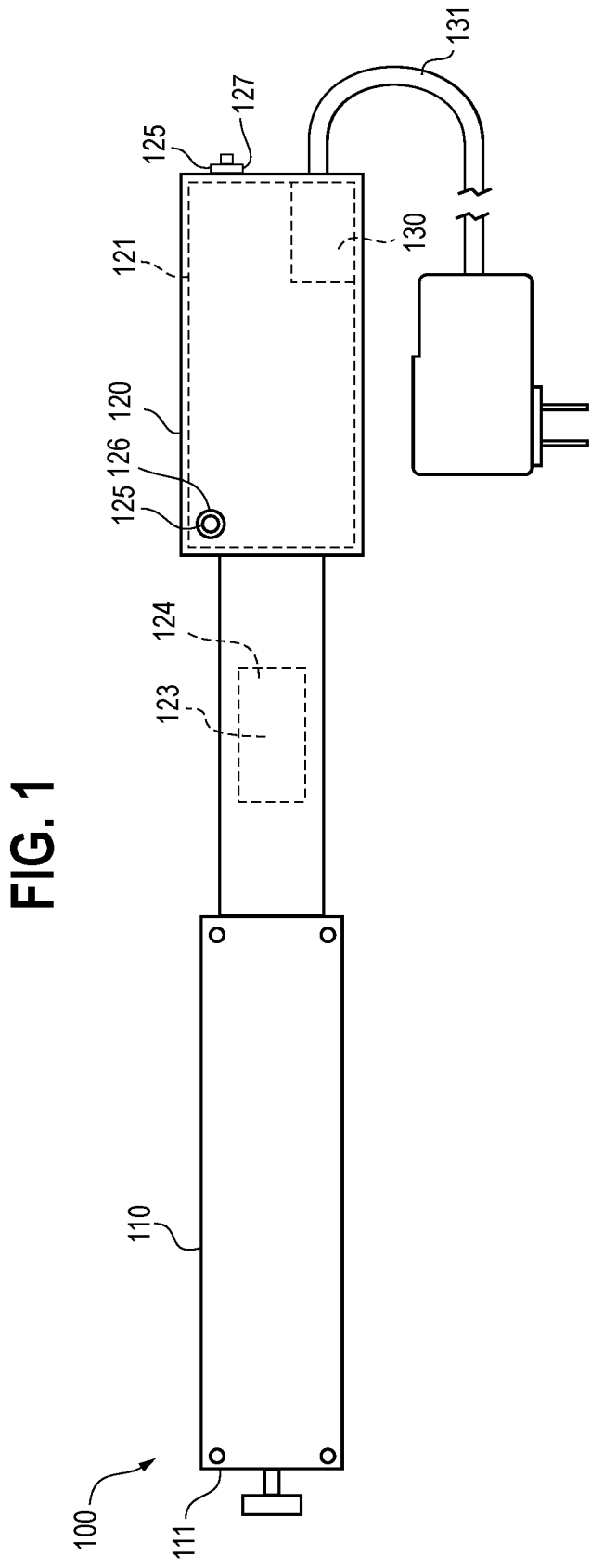

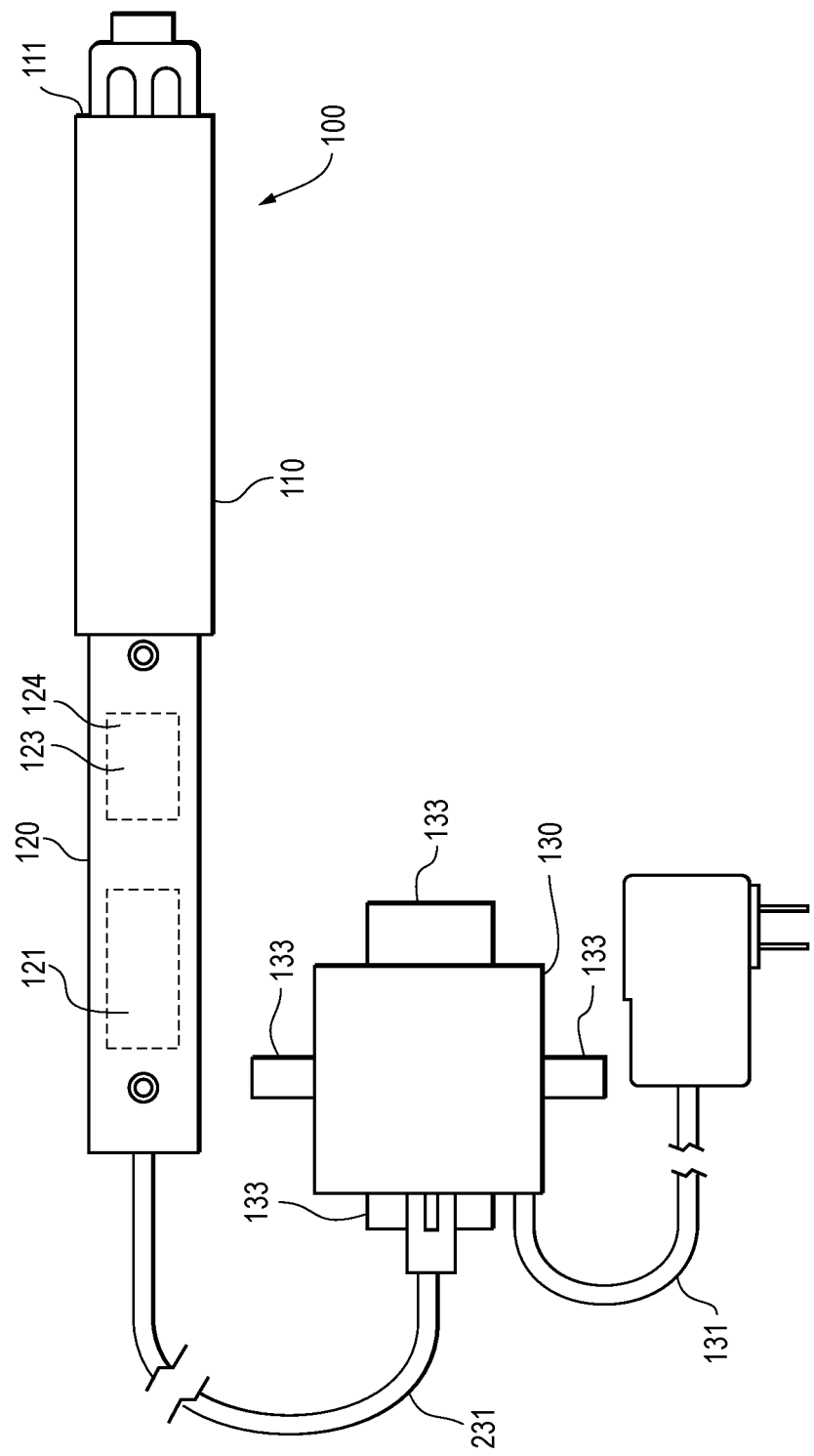

INJECTION DEVICE AND METHOD OF MAKING AND USING THE SAME

TECHNICAL FIELD

The presently-disclosed subject matter generally relates to an injection device and methods of making and using the same. More specifically, the presently-disclosed subject matter relates to a multiple syringe automated injector and methods of making and using the same.

BACKGROUND

Based upon recent estimates, at least 16 billion injections are administered each year. These injections are for various different applications, including vaccination, immunization, disease treatment, and other therapeutic purposes. While a majority of these are administered by health care professionals, the professional, the setting, and the type of injection varies widely depending upon the purpose.

In certain instances, such as during research and for treatment of some conditions, multiple injections are required. These multiple injections may be spread out over time or may be administered in a single continuous session. Typically, the effectiveness of these injections is reduced by inconsistent injection depth, amount, and/or distribution. Additionally, the session can be both time consuming and painful as each injection has to be individually administered by hand.

Accordingly, there remains a need for a device that provides multiple efficient, consistent, and/or uniform injections.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently-disclosed subject matter is directed to an injection device including a base portion including a body section and a control section, at least one bracket secured to the body section, an articulation element secured to the control section, and a pusher plate coupled to the articulation element, wherein the articulation element moves the pusher plate with respect to the base portion. In some embodiments, the device includes an end protector. In one embodiment, the end protector includes a fixed portion secured to one of the at least one brackets, a moveable portion supported by and moveable with respect to the fixed portion, and an end pad attached to the moveable portion. In another embodiment, the end protector comprises a first position where the moveable portion is fully extended with respect to the fixed portion, and a second position where the moveable portion is at least partially retracted with respect to the fixed portion. In one embodiment, the end protector includes an end plate having at least two openings formed therein.

In some embodiments, the device includes a controller electrically coupled to the articulation element. In some embodiments, the device includes a power element electrically coupled to at least the controller. In one embodiment, the power element is attached to the body portion. In one embodiment, the power element is separate from the body portion. In some embodiments, the device includes at least one control element electrically coupled to the controller. In one embodiment, the control element is arranged and disposed to activate the articulation element through the controller.

In some embodiments, the device includes at least two syringes removably positioned within the body section. In one embodiment, the at least two syringes are removably attached to a syringe holder. In another embodiment, the syringe holder is removably positioned within the body section. In another embodiment, the syringe holder is permanently secured to the body section. In some embodiments, each syringe includes a reservoir, a plunger extending from the reservoir towards the pusher plate, and a needle extending from the reservoir towards an injection end of the device.

Also provided herein, in some embodiments, is a method of injecting a patient, the method including positioning at least two syringes in the injection device, placing an injection end of the injection device in contact with an injection site on the patient, and activating the articulation element, wherein activating the articulation element moves the pusher plate towards the at least two syringes, depressing a plunger and dispensing a fluid from the at least two syringes. In some embodiments, the method includes, prior to the activating of the articulation element, pressing the injection end against the injection site on the patient and at least partially retracting an end protector of the injection device. In some embodiments, the method includes at least one of dispensing mixtures of fluid from multiple reservoirs, dispensing different amounts of fluid from different reservoirs, and a combination thereof. In some embodiments, the activating of the articulation element is automated by a controller.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1 shows an image of a multiple syringe automated injector, according to an embodiment of the disclosure.

FIG. 2 shows an image of a multiple syringe automated injector, according to another embodiment of the disclosure.

DESCRIPTION OF EXEMPLARY EMBODIMENTS

Figure 3A:
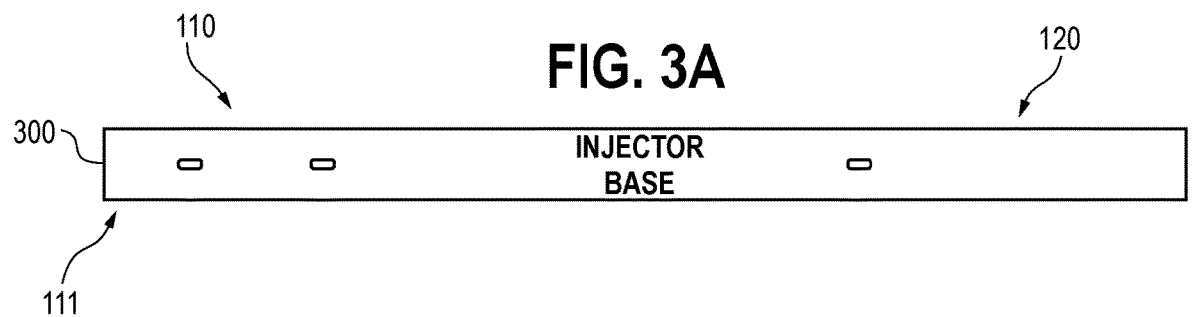
FIGS. 3A-C show images illustrating different views of a base portion of the injection device. (A) Shows a top view of a base portion. (B) Shows a side view of a body section of the base portion with brackets attached thereto. (C) Shows a front view of a bracket secured to the base portion.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites, and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

When open-ended terms such as "including" or 'including, but not limited to" are used, there may be other non-enumerated members of a list that would be suitable for the making, using or sale of any embodiment thereof.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes an injection device 100 (FIGS. 1-2). The injection device 100 comprises a body section 110 and a control section 120. In some embodiments, the control section 120 houses a controller 121, which is arranged and disposed to control the functioning of the injection device 100. For example, in one embodiment, the controller 121 is electrically coupled to an articulation element 123, such as a motor 124. In another embodiment, the controller 121 is electrically coupled to one or more control elements 125. In a further embodiment, the one or more control elements 125 include, but are not limited to, an inject button 126 and a return button 127. In such embodiments, pressing the inject button 126 or the return button 127 sends a signal to the controller 121, which activates the motor 124 to facilitate injection or retraction, respectively. Although described in terms of an inject button 126 and a return button 127, as will be appreciated by those skilled in the art the disclosure is not so limited and may include any other suitable control element 125, such as, but not limited to, one or more switches, knobs, dials, or other elements capable of signaling the controller 121 to activate the articulation element 123.

The injection device 100 also includes a power element 130, which is arranged and disposed to provide electricity to the controller 121, the articulation element 123, and/or any other element of the injection device 100 that requires electrical power to operate. In some embodiments, as illustrated in FIG. 1, the power element 130 is attached directly to and/or contained within the control section 120. In one such embodiment, the power element 130 is electrically coupled to a power cord 131, which is arranged and disposed to couple with any suitable power source, such as an outlet. When the power cord 131 is coupled with a power source, the power element 130 distributes power to the injection device 100 directly from the power source and/or acts as a battery to store power from the power source for distribution later. Additionally or alternatively, the power element 130 may be charged through induction charging while within and/or attached to the control section 120, or may be removable from the control section 120 for charging in a separate charging unit.

Referring to FIG. 2, in some embodiments, the power element 130 is electrically coupled to the control section 120 through a control cable 231, but otherwise physically separate therefrom. This physical separation of the power element 130 from the control section 120 reduces the weight and/or size of the injection device 100 during use, which increases portability, usability, and/or maneuverability thereof. Additionally, in some embodiments, the power element 130 may be secured and/or mounted to a surface through one or more mounting elements 133, with the control section 120 being movable relative thereto.

Figure 3B:
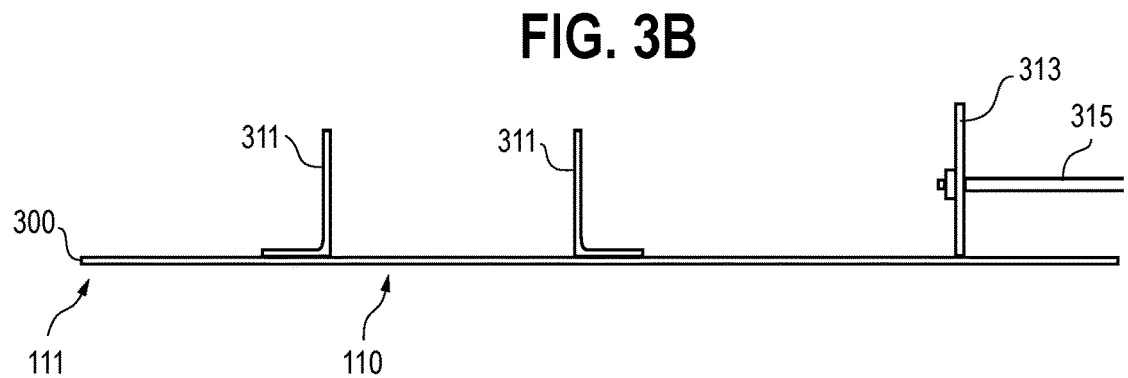
Figure 3C:
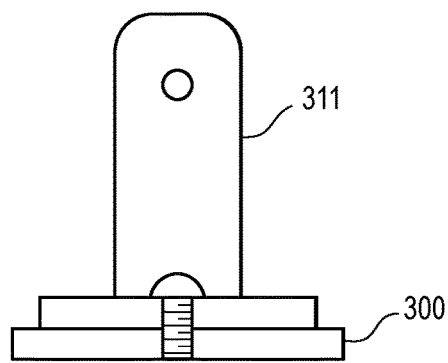

Turning to FIG. 3A, in some embodiments, the body section 110 and the control section 120 are both formed on a base portion 300 of the injection device 100. In one embodiment, as illustrated in to FIG. 3B, the body section 110 includes one or more brackets 311 and a pusher plate 313. In another embodiment, the one or more brackets 311 are secured to a surface of the base portion 300 (FIG. 3C). In a further embodiment, each of the one or more brackets 311 is either fixed to the surface of the base portion 300 in a stationary position or movably attached to the surface of the base portion 300. Additionally or alternatively, the pusher plate 313 is movably positioned between the one or more brackets 311 and the control section 120.

In some embodiments, the pusher plate 313 is physically coupled to the articulation element 123 through any suitable connection member 315. Suitable connection members 315 include any member suitable for supporting and/or moving the pusher plate 313 upon activation of the articulation element 123. Such members include, but are not limited to, a rod, a screw, a plate, a post, or any combination thereof. For example, in one embodiment, the connection member 315 includes a rod attached to the pusher plate 313 and coupled to the articulation element 123. In another embodiment, activation of the articulation element 123 to facilitate injection, such as through pressing the inject button 126, extends the rod and moves the pusher plate 313 towards an injection end 111 of the body section 110. Conversely, activation of the articulation element 123 to facilitate retraction, such as through pressing the return button 127, retracts the rod and moves the pusher plate 313 away from the injection end 111 of the body section 110. Additionally or alternatively, in some embodiments, the articulation element 123 may be programmed to automatically return the pusher plate 313 to the original retracted position after completing a final/designated injection.

Figure 4A:
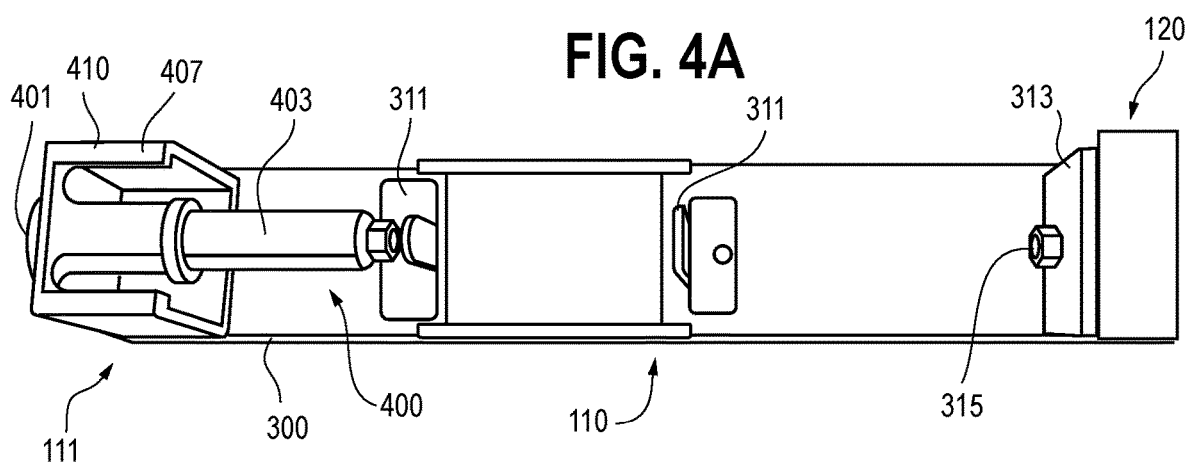
FIGS. 4A-D show images of an end protection device. (A) Shows a top perspective view of an end protection device attached to a base portion. (B) Shows a top view of an end protection device. (C) Shows a front view of an end protector. (D) Shows a top view of an end protector.
Figure 4B:
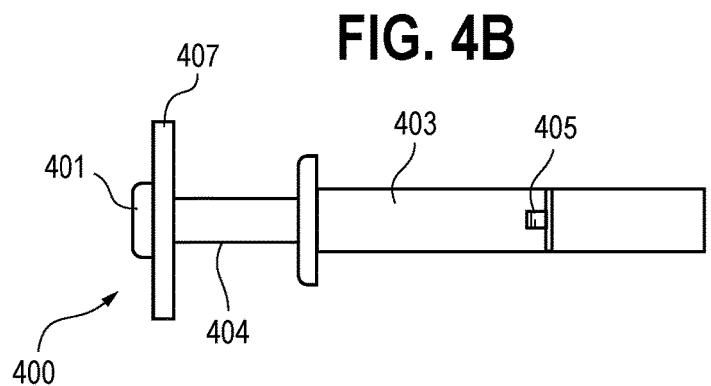

Referring to FIGS. 4A-B, in some embodiments, the injection device 100 also includes an end protector 400. In one embodiment, the end protector 400 includes an end pad 401 arranged and disposed to contact a patient during use of the injection device 100. The end pad 401 includes any soft and/or elastic material suitable for cushioning contact between the injection device 100 and a patient. In another embodiment, the end protector 400 includes a fixed portion 403 and a movable portion 404. The fixed portion 403 is secured to the body section 110 with any suitable attachment feature 405 (FIG. 4B), such as, but not limited to, a threaded recess that receives a screw or other threaded post extending from or through the bracket 311. The movable portion 404 is supported by, and movable with respect to, the fixed portion 403. For example, the movable portion 404 may slide within and extend from the fixed portion 403.

Figure 4C:
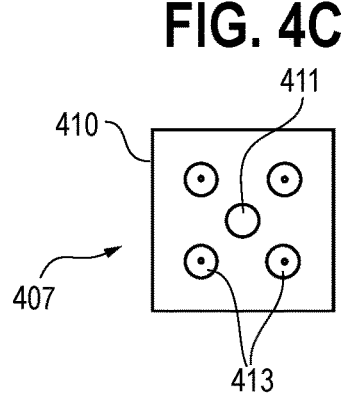
Figure 4D:
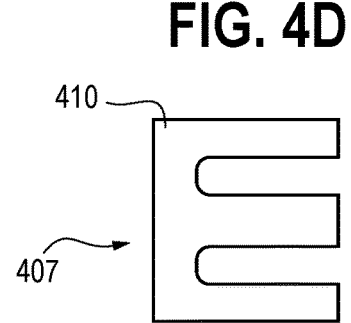

Additionally or alternatively, as illustrated in FIGS. 4A-D, the end protector 400 optionally includes an end plate 407. In one embodiment, the end plate 407 is attached to the end protector 400, between the end pad 401 and the movable portion 404. In another embodiment, the end pad 401 and the end plate 407 move with the movable portion 404 as it retracts and extends from the fixed portion 403. The end plate 407 includes any suitable shape and/or size for covering the injection end 111 of the body section 110. For example, in one embodiment, as illustrated in FIG. 4C, the end plate 407 is a solid sheet having a mounting hole 411 for attachment to the end protector 400 and at least one opening 413 arranged and disposed to permit passage of a needle there through. Referring to FIGS. 4A and D, in another embodiment, the end plate 407 includes an open box 410. In such embodiments, the open box 410 includes an open back facing the body section 110, a solid bottom facing the base portion 300, solid left and right sides, a partially open top, and a front formed from the solid sheet of FIG. 4C.

Figure 5A:
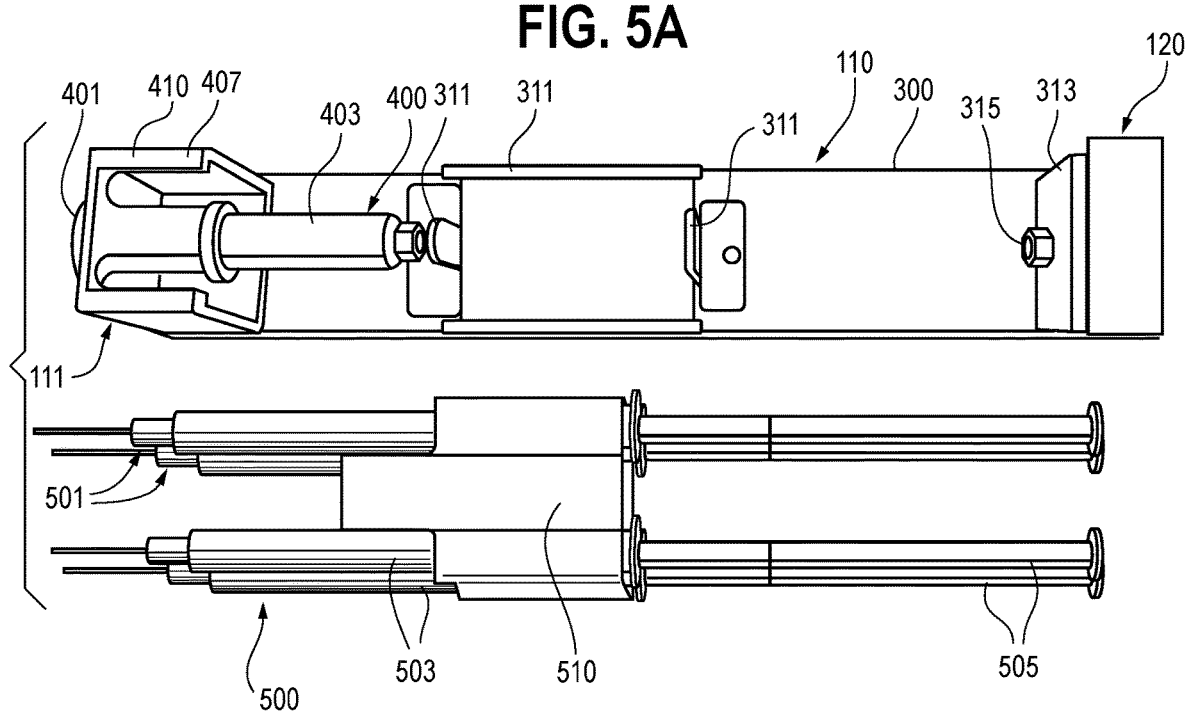
FIGS. 5A-B show images illustrating a syringe holder with syringes before and after being inserted into the body section. (A) Shows an image of the syringe holder and syringes before insertion into the body section. (B) Shows an image of the syringe holder and syringes after insertion into the body section.
Figure 5B:
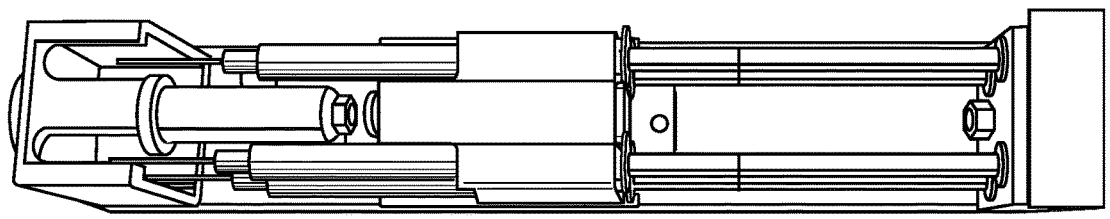

Turning now to FIGS. 5A-B, in some embodiments, the injection device 100 also includes at least two syringes 500. In one embodiment, each syringe 500 includes a needle 501, a reservoir 503, and a plunger 505. Each needle 501 extends from the reservoir 503 towards the injection end 111, and each plunger 505 extends from the reservoir 503 towards the pusher plate 313. In some embodiments, when extended by the articulation element 123, the pusher plate 313 contacts and subsequently depresses the plunger(s) 505, which dispenses a fluid from the reservoir(s) 503. Additionally or alternatively, in some embodiments, the end protector 400 includes a first position and a second position. In one embodiment, when in the first position, the end protector 400 extends past the tip of each needle 501. In another embodiment, when in the second position, the end protector 400 is retracted such that at least the tip of each needle 501 passes through the opening(s) 413 in the end plate 407, when present, and past the end pad 401. In a further embodiment, when in the first position, the end protector 400 substantially protects the needles 501 from contacting a surface for injection while, when in the second position, the end protector 400 exposes the needles 501 to permit contacting a surface for injection.

Figure 6A:
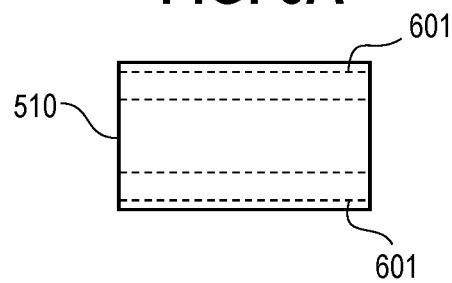
FIGS. 6A-C show images of a syringe holder according to an embodiment of the disclosure. (A) Shows a top view of a syringe holder having elongated clasps extending the full length of the holder without syringes inserted therein. (B) Shows a side view of a syringe holder having elongated clasps extending partially along the length of holder with syringes inserted therein. (C) Shows a top view of a syringe holder of (B).
Figure 6B:
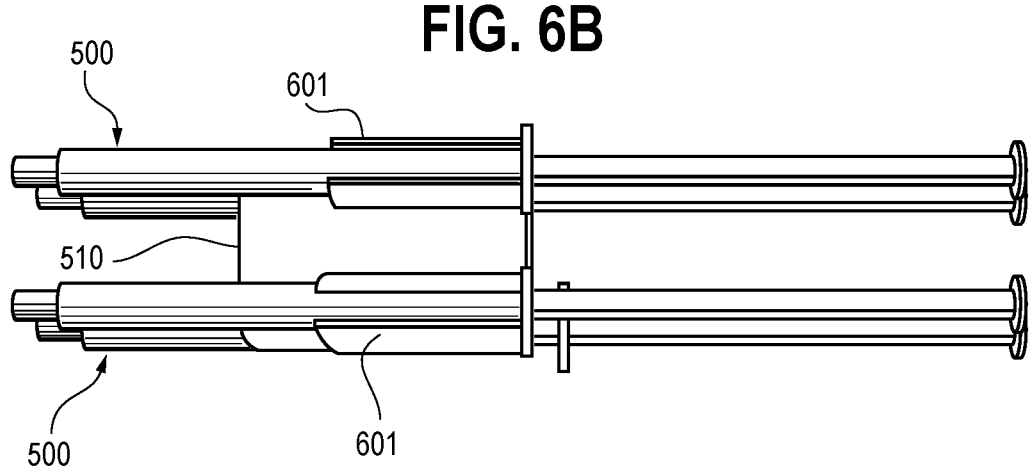
Figure 6C:
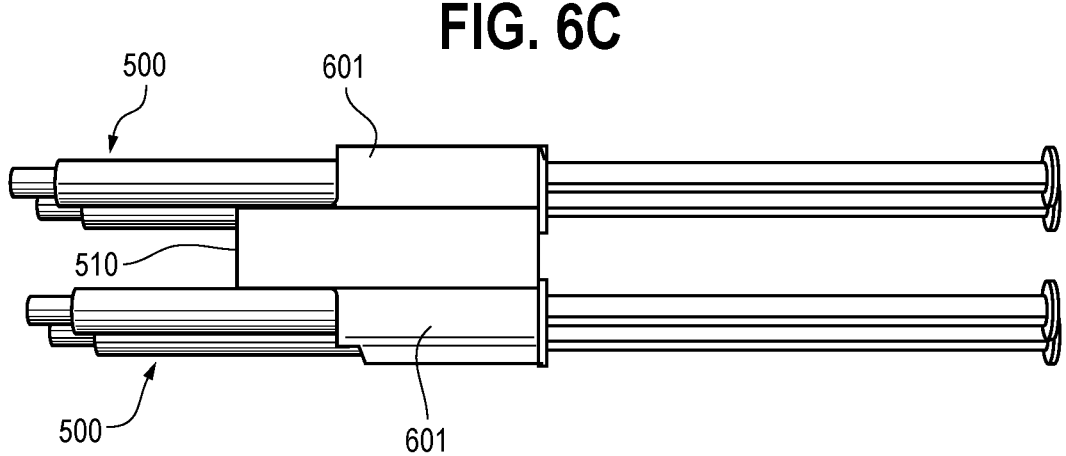
Figure 7A:
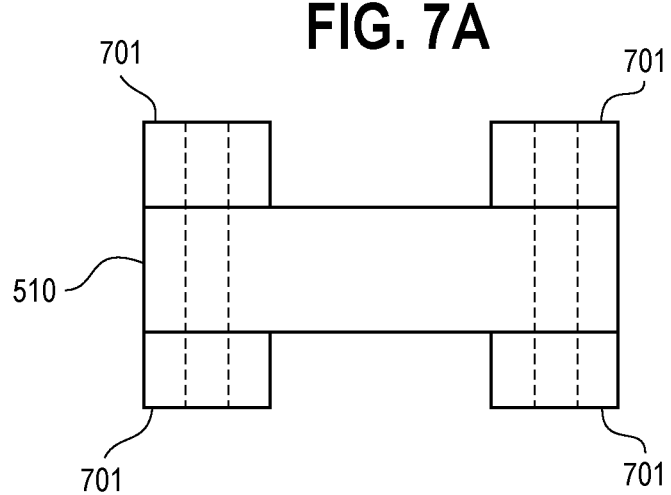
FIGS. 7A-C show images of a syringe holder according to an embodiment of the disclosure. (A) Shows a top view of a syringe holder having multiple clasps along the length thereof without syringes inserted therein. (B) Shows a front view of the syringe holder of (A). (C) Shows a side view of the syringe holder of (A).
Figure 7B:
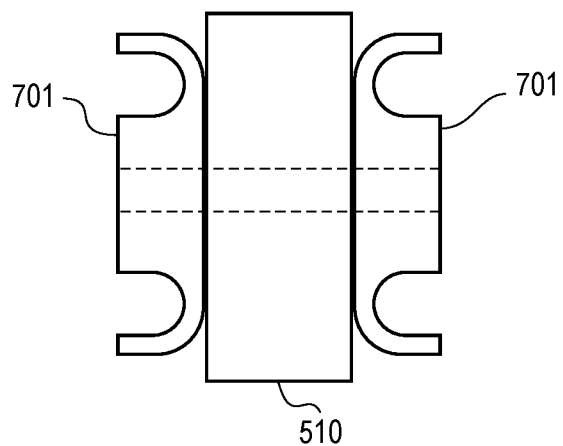
Figure 7C:
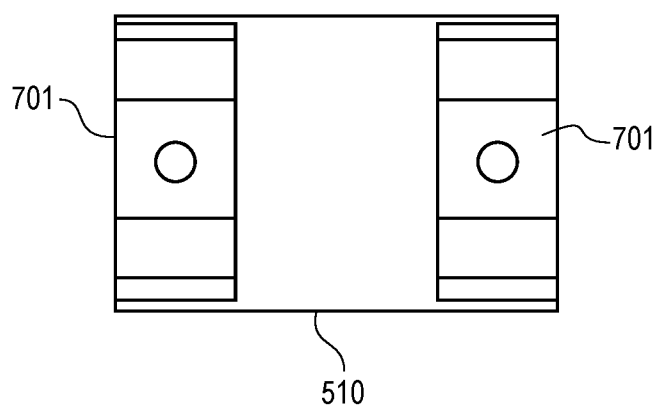

In some embodiments, the syringes 500 are removably positioned within the body section 110. As used herein, the term "removably" refers to an article being held in place without structural modification, such that one or more articles can be repeatedly placed and removed in the same position without damaging the article. For example, in one embodiment, the syringes 500 are removably secured to a syringe holder or cassette 510 using elongated "C" shaped clasps 601 (FIGS. 6A-C) and/or multiple "C" shaped clasps 701 (FIGS. 7A-7C). In another embodiment, the syringe holder or cassette 510 is removably secured to the body section 110 by the brackets 311, which restrict movement of the syringe holder or cassette 510 on the base portion 300. For example, the syringe holder 510 may be slidably positioned between the brackets 311 on the base portion 300. In a further embodiment, the position of the brackets 311 may be adjusted to accommodate cassettes 510 of different sizes. Adjusting the position of the brackets 311 may include, but is not limited to, loosening and tightening one or more screws extending through slots or elongated holes in the base portion 300 to move and set the fixed position of the bracket(s) 311, respectively.

Although discussed above primarily with respect to multiple brackets 311 restricting movement of the removable syringe holder or cassette 510, as will be understood by those skilled in the art, the disclosure is not so limited and may include a single bracket 311 or multiple brackets 311 having one or more features arranged and disposed to engage the syringe holder or cassette 510. For example, in some embodiments, the injection device 100 only includes a single bracket 311. In such embodiments, the syringe holder 510 engages with the one or more features on the bracket 311 and/or the surface of the base portion 300 to reversibly secure the syringe holder 510 thereto. Suitable securing features may include, but are not limited to, a shaped recess on the bracket 311 and/or surface of the base portion 300 for receiving a correspondingly shaped protrusion on the syringe holder 510, or vice versa; correspondingly shaped tongue and groove features; a mating locking mechanism, or a combination thereof. Similarly, the disclosure is not limited to a removable syringe holder 510, and expressly includes embodiments where the syringe holder 510 is integral with or permanently attached to the base portion 300. In such embodiments, the syringes 500 are removably attached to the syringe holder 510 according to any one or more of the embodiments disclosed herein. Additionally or alternatively, the brackets 311 may be arranged and disposed to removably secure one or more of the syringes 500 directly, such as, for example, through clamps or features formed directly on the brackets 311 to engage the syringes 500.

As will also be appreciated by those skilled in the art, the at least two syringes 500 include any suitable number of syringes 500 for dispensing and/or injecting a desired about of fluid. For example, the number of syringes 500 in the injection device 100 may include 2, 3, 4, 5, 6, 7, 8, 9, 10, more than 10, between 2 and 10, between 2 and 8, between 2 and 6, between 3 and 5, or any combination, sub-combination, range, or sub-range thereof. In some embodiments, the number of needles 501, reservoirs 503, and/or plungers 505 may differ from each other. In one embodiment, for example, the injection device 100 includes at least two needles 501 in fluid communication with a single reservoir 503 having a single plunger 505. Where multiple needles 501 are in fluid communication with a single reservoir 503, the needles 501 and reservoir 503 together are considered a single syringe 500 according to the instant disclosure. Such embodiments may be provided alone, or in combination with at least one other syringe 500. Accordingly, in addition to embodiments of the injection device 100 including at least two syringes 500, the injection device 100 may include embodiments having one syringe 500 with at least two needles 501. The at least two needles 501 includes any suitable number of needles 501 for a desired number of injection sites, such as, but not limited to, 2, 3, 4, 5, 6, 7, 8, 9, 10, more than 10, between 2 and 10, between 2 and 8, between 2 and 6, between 3 and 5, or any combination, sub-combination, range, or sub-range thereof. Additionally or alternatively, the injection device 100 may include multiple reservoirs 503 in fluid communication with one needle 501. In such embodiments, a fluid in each reservoir 503 may be simultaneously or sequentially delivered to the needle 501 in common fluid communication therewith. Furthermore, a single plunger 505 may be coupled to multiple reservoirs 503, such that depressing the plunger 505 simultaneously dispenses the contents of each reservoir 503 coupled thereto.

The size of the needles 501, reservoirs 503, and/or plungers 505 may also be the same or different. In some embodiments, the needles 501 are the same gauge/length, and the reservoirs 503 and plungers 505, when more than one is present, are the same size/capacity and size/length, respectively. In some embodiments, at least one of the needles 501 is a different length from the other needles 501 while the reservoirs 503 are the same size/capacity and the plungers 505 are the same size/length. In such embodiments, the different length of the needles 501 provides a different depth of injection. In some embodiments, at least one plunger 505 is a different length than the other plunger(s) 505. In such embodiments, when the reservoirs 503 are the same size/capacity, the shorter plunger 505 will dispense a decreased amount of fluid when all plungers 505 are depressed to the same position. In some embodiments, at least one of the needles 501 is a different gauge from the other needles 501. As will be appreciated by those skilled in the art, when the reservoirs 503 are the same size/capacity, the plunger(s) 505 are depressed at the same rate, and at least one of the needles 501 has a different gauge, the fluid will be dispensed through the different gauges at different pressures (i.e., fluid will be dispensed through smaller diameter needles (higher gauge) at a higher pressure than larger diameter needles (lower gauge)). Therefore, in one embodiment, the size/capacity of a reservoir 503 in fluid communication with a needle 501 having a different gauge is adjusted accordingly (e.g., the reservoir in fluid communication with the higher gauge needle(s) is smaller than the reservoir in fluid communication with the lower gauge needle(s)). In such embodiments, the needle(s) 501 with a different gauge/reservoir 503 will dispense a different amount of fluid at the same rate and in the same amount of time as the other needle(s) 501/reservoir(s) 503.

In some embodiments, the syringes 500 or at least a portion thereof are disposable. In some embodiments, at least a portion of the syringes 500 is reusable. For example, in one embodiment, the needle 501 is detachable from the reservoir 503 and plunger 505, the needle 501 being disposable and the reservoir 503 and plunger 505 being reusable. Additionally or alternatively, the syringe holder or cassette 510 may be disposable or reusable. Suitable reusable materials include any material suitable for repeated sterilization following each use, such as, but not limited to, metal, rubber, polymer, plastic, any other material suitable for sterilization, or a combination thereof.

Also provided herein, in some embodiments, is a method of injecting a patient using the injection device 100. The method includes providing the syringe(s) 500 in the body section 110, placing the injection end 111 of the injection device 100 in contact with an injection site on the patient, and activating the articulation element 123. In one embodiment, providing the syringe(s) 500 in the body section 110 includes positioning the syringe(s) 500 such that the needles 501 extend toward the injection end 111 and the plunger(s) 505 extend towards the pusher plate 313. In another embodiment, activating the articulation element 123 includes manipulating one of the control elements 125, such as the injection button 126, such that the articulation element 123 moves the pusher plate 313 away from the control section 120 and towards the injection end 111. The movement of the pusher plate 313 depresses the plunger(s) 505 of the syringe (s) 500, which dispenses fluid from the reservoir(s) 503 thereof. As will be appreciated by those skilled in the art, in some embodiments, the method may include dispensing mixtures of fluid from multiple reservoirs (e.g., multiple reservoirs in fluid communication with a single needle), dispensing different amounts of fluid from different reservoirs (e.g., different sized reservoirs/needles and/or different length plungers), or a combination thereof.

Figure 8:
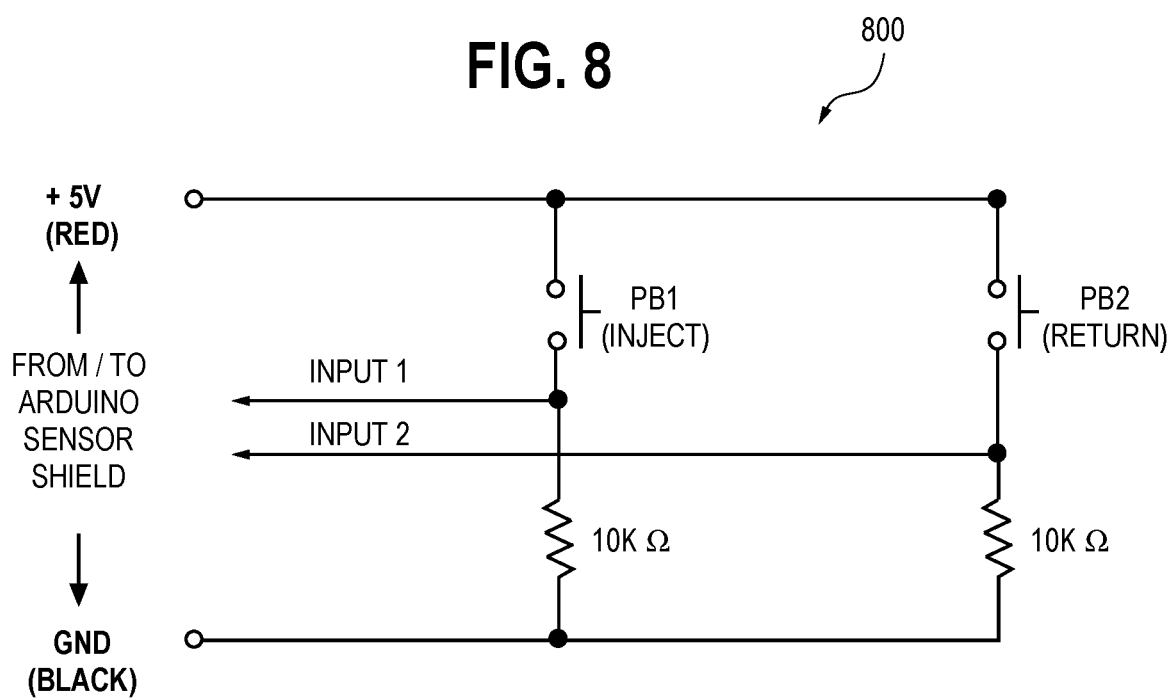
FIG. 8 shows a wiring diagram for a multiple syringe automated injector.

In one embodiment, the activation of the articulation element 123 is automated by the controller. For example, in another embodiment, the injection device 100 is programmed to dispense a specific amount of fluid at a specific rate by automating the movements of the pusher plate 313 through the controller 121. In such embodiments, the controller 121 includes any suitable element for automating dispensing and/or injection, such as, but not limited to, a processor. Alternatively, the articulation element 123 may be activated only as long as the control elements 125 are pressed. An example wiring diagram 800 illustrating the control elements 125 electrically coupled to the controller 121 is shown in FIG. 8.

In some embodiments, prior to activating the articulation element 123, the method includes pressing the injection end 111/end pad 401 against the patient to at least partially retract the end protector 400. The partial retraction of the end protector 400 causes the needles 501 of the syringe(s) 500 to extend through the openings 413 of the optional end plate 407, past the end pad 401, and into the patient's skin. In such embodiments, the end protector 400 may provide resistance to the retraction of the end protector 400 and/or limits the amount of retraction. For example, the fixed portion 403 may include a spring that provides resistance to the retraction of the movable portion 404, and/or the fixed portion 403 may be filled with a fluid such that the fixed portion 403 and the movable portion 404 form a piston. Additionally or alternatively, the retraction of the end protector 400 may be automated, such that the end protector 400 retracts the movable portion 404 prior to activating the articulation element 123. Automation of the end protector 400 is controlled by the controller 121, and may include retracting the end protector 400 by a set amount, which may be different between injections (e.g., for different length needles and/or different depth of injection).

After injection, the method may include extending the end protector 400 and/or retracting the pusher plate 313. In one embodiment, retracting the pusher plate 313 includes manipulating one of the control elements 125, such as the return button 127, such that the articulation element 123 moves the pusher plate 313 towards the control section 120 and away from the injection end 111. Following retraction of the pusher plate 313, the syringe(s) 500 may be removed from the body section 110 and the method may be repeated for subsequent injections. In certain embodiments, where all components are disposable, the syringe holder 510, including the syringe(s) 500, is simply removed and disposed of. In other embodiments, where some or all of the components are reusable, the syringe holder 510 is removed from the injection device 100, any disposable components are removed and disposed of, and the remaining reusable components are sterilized prior to any subsequent injection. As will be appreciated by those skilled in the art, the individual reusable components may be removed and sterilized separately, or they may remain secured and be sterilized together. For example, where a reusable syringe holder 510 includes reusable reservoir(s) 503, reusable plunger(s) 505, and disposable needles 501, after removing and disposing of the needles 501 the syringe holder 510 may be sterilized with the reservoir(s) 503 and plunger(s) 505 still secured thereto, or the reservoir(s) 503 and plunger(s) 505 may be removed and sterilized separately. In certain embodiments, the reusable reservoir(s) 503 and/or plunger(s) 505 may be integrated into the reusable syringe holder 510, such that only the needles 501 need be removed prior to sterilization and replaced with new needles thereafter.

By fixing the position of the syringe(s) 500 within the body section 110, and including an end protector 400, as described herein, the injection device 100 provides a consistent and/or uniform depth of injection from each needle 501 and/or each repeated injection. Additionally, the positioning of the syringe(s) 500 and/or the automation from the controller 121 provides uniform injection distribution of the fluid. Furthermore, the injection device 100 provides increased efficiency, permitting multiple simultaneous injections at a set depth and set amount, which is not possible manually. Accordingly, the injection device may be used to provide efficient, consistent, and/or uniform injection of any suitable fluid to any suitable area. Suitable fluids include, but are not limited to, platelet rich plasma (PRP). Suitable areas include, but are not limited to, the scalp.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

This example describes one type of injection encompassed by the disclosure above. In this example, the injection device is a quad injector, including four needles in fluid communication with a single reservoir. The reservoir is filled with PRP, which is simultaneously injected into the scalp through all four needles upon retraction of the end protector and depression of the plunger. Each injection delivers exactly 0.2 cc's of PRP, allowing for the injection of 4 cc's in less than 1 minute.

Injection of PRP using the device as described in this example removes variables concerning depth of injection as well as uniform distribution of PRP. This is valuable not only for clinical aspects but also for research purposes. Additionally, the device increases the efficiency of PRP injection by delivering more PRP in a shorter amount of time and with more consistent delivery as compared to manual delivery. This provides better results to the patient.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:
1. An injection device, comprising:
a base portion including a body section and a control section:
at least one bracket secured to the body section;
an articulation element secured to the control section;
a pusher plate coupled to the articulation element; and an end protector secured to the body section, the end protector comprising:
  a fixed portion secured to one of the at least one brackets;
  a moveable portion supported by and moveable with respect to the fixed portion; and
  an end pad attached to the moveable portion;
wherein the articulation element moves the pusher plate with respect to the base portion; and
wherein the end protector includes a first position that extends past the tip of a needle in the device and a second position that exposes the tip of the needle.

2. The device of claim 1, wherein, when in the first position the moveable portion is fully extended with respect to the fixed portion, and, when in the second position, the moveable portion is at least partially retracted with respect to the fixed portion.

3. The device of claim 1, wherein the end protector further comprises an end plate having at least two openings formed therein.

4. The device of claim 1, further comprising a controller electrically coupled to the articulation element.

5. The device of claim 4, further comprising a power element electrically coupled to at least the controller.

6. The device of claim 5, wherein the power element is attached to the control section.

7. The device of claim 5, wherein the power element is separate from the control section.

8. The device of claim 4, further comprising at least one control element electrically coupled to the controller.

9. The device of claim 8, wherein the control element is arranged and disposed to activate the articulation element through the controller.

10. The device of claim 1, further comprising at least two syringes removably positioned within the body section.

11. The device of claim 10, wherein the at least two syringes are removably attached to a syringe holder.

12. The device of claim 11, wherein the syringe holder is removably positioned within the body section.

13. The device of claim 11, wherein the syringe holder is permanently secured to the body section.

14. The device of claim 10, wherein each of the at least two syringes comprises:
  a reservoir;
  a plunger extending from the reservoir towards the pusher plate; and
  a needle extending from the reservoir towards an injection end of the device.

15. A method of injecting a patient, the method comprising:
  positioning at least two syringes in the injection device of claim 1;
  placing an injection end of the injection device in contact with an injection site on the patient; and
  activating the articulation element;
  wherein activating the articulation element moves the pusher plate towards the at least two syringes, depressing a plunger and dispensing a fluid from the at least two syringes.

16. The method of claim 15, further comprising, prior to the activating of the articulation element, pressing the injection end against the injection site on the patient and at least partially retracting an end protector of the injection device.

17. The method of claim 15, further comprising at least one of dispensing mixtures of fluid from multiple reservoirs, dispensing different amounts of fluid from different reservoirs, and a combination thereof.

18. The method of claim 15, wherein the activating of the articulation element is automated by a controller.

* * * * *